United States Patent
Isobe et al.

(10) Patent No.: US 9,168,213 B2
(45) Date of Patent: Oct. 27, 2015

(54) ORAL COMPOSITION

(75) Inventors: Tsutomu Isobe, Tochigi (JP); Gen Nakauchi, Inzai (JP); Yoshiyuki Eshita, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/008,724

(22) PCT Filed: Apr. 6, 2012

(86) PCT No.: PCT/JP2012/059569
§ 371 (c)(1),
(2), (4) Date: Sep. 30, 2013

(87) PCT Pub. No.: WO2012/137941
PCT Pub. Date: Oct. 11, 2012

(65) Prior Publication Data
US 2014/0017180 A1 Jan. 16, 2014

(30) Foreign Application Priority Data
Apr. 8, 2011 (JP) ................................. 2011-085968

(51) Int. Cl.
| | |
|---|---|
| *A61Q 11/00* | (2006.01) |
| *A61K 8/55* | (2006.01) |
| *A61K 6/00* | (2006.01) |
| *A61K 8/69* | (2006.01) |
| *A61K 8/24* | (2006.01) |

(52) U.S. Cl.
CPC ... *A61K 8/55* (2013.01); *A61K 8/24* (2013.01); *A61Q 11/00* (2013.01)

(58) Field of Classification Search
CPC ............ A61Q 11/00; A61K 8/55; A61K 6/00
USPC ............... 424/57, 9.36, 49, 52, 603, 605, 682
See application file for complete search history.

(56) References Cited

U.S. PATENT DOCUMENTS

| | | | |
|---|---|---|---|
| 4,259,316 A | 3/1981 | Nakashima et al. | |
| 4,335,102 A | 6/1982 | Nakashima et al. | |
| 2007/0122357 A1 | 5/2007 | Glandorf | |
| 2007/0122358 A1 | 5/2007 | Wang et al. | |
| 2007/0122359 A1 | 5/2007 | Wang et al. | |
| 2007/0183991 A1* | 8/2007 | Katou et al. | 424/58 |
| 2008/0175801 A1* | 7/2008 | Ramji | 424/53 |
| 2010/0135921 A1* | 6/2010 | Hughes et al. | 424/49 |
| 2011/0223119 A1 | 9/2011 | Isobe et al. | |

FOREIGN PATENT DOCUMENTS

| | | |
|---|---|---|
| CN | 1115636 A | 1/1996 |
| CN | 1593376 A | 3/2005 |
| CN | 101330900 A | 12/2008 |
| CN | 1013166572 A | 12/2008 |
| CN | 101690699 A | 4/2010 |
| JP | 56-18913 A | 2/1981 |
| JP | 56-045407 A | 4/1981 |
| JP | 11-349460 A | 12/1999 |
| JP | 2003-335646 A | 11/2003 |
| JP | 2009-513695 A | 4/2009 |
| JP | 2009-520829 A | 5/2009 |
| JP | 2010-120880 A | 6/2010 |
| WO | WO 2007/063506 A2 | 6/2007 |
| WO | WO 2007/063507 A2 | 6/2007 |
| WO | WO 2007/076001 A2 | 7/2007 |
| WO | WO 2010/058522 A1 | 5/2010 |

OTHER PUBLICATIONS

International Search Report (ISR) for PCT/JP2012/059569; I.A. fd: Apr. 6, 2012, mailed Jul. 3, 2012 from the Japanese Patent Office, Tokyo, Japan.
International Preliminary Report on Patentability (IPRP), Chapter I of the Patent Cooperation Treaty, including the Written Opinion for PCT/JP2012/059569; I.A. fd: Apr. 6, 2012,, issued Oct. 8, 2013, by the International Bureau of WIPO, Geneva, Switzerland.
Extended European search report for EP patent application No. 12768299.5, including the supplementary European search report and the European search opinion, dated Feb. 20, 2015.

* cited by examiner

*Primary Examiner* — Frederick Krass
*Assistant Examiner* — Tracy Liu
(74) *Attorney, Agent, or Firm* — Sterne, Kessler, Goldstein & Fox P.L.L.C.

(57) ABSTRACT

Provided is an oral composition which is excellent in a gloss imparting effect on teeth.
An oral composition, which comprises the following components (A) and (B):
(A) 0.01 to 3% by mass of phytic acid or a salt thereof, and
(B) 0.01 to 3% by mass of pyrophosphoric acid or a salt thereof, does not comprise a polyvalent cation or comprises a polyvalent cation in an amount of less than 0.1-fold mol relative to phytic acid, has pH 5.5 to 6.5 when diluted with water to 30% by mass, has the mass ratio (B/A) between the component (A) and the component (B) is 0.2 to 3.0, and does not comprise a fluoride or has the fluoride content of less than 500 ppm in terms of fluorine atoms.

20 Claims, 3 Drawing Sheets

ORAL COMPOSITION

FIELD OF THE INVENTION

The present invention relates to an oral composition which is capable of imparting gloss to teeth.

BACKGROUND OF THE INVENTION

Human teeth are stained by adhesion of various staining substances on their surfaces along with calculus and plaque, and the gloss of teeth also decreases. These staining and decrease in gloss are not cosmetically desirable, and various means to whiten teeth are developed.

It has been known that phytic acid has activities such as removal of tobacco tar, a suppressive effect against calculus and stabilization of stannous fluoride, and a cleansing agent and a dentifrice, each containing phytic acid, have been reported (Patent Document 1). A dentifrice composition in which a tin compound (Patent Document 2), zeolite (Patent Document 3), particles having specific collapse strength (Patent Document 4) or the like is mixed along with phytic acid has been also reported. Further, the present applicant reported that although minute solid matter with the height of less than 1 μm which adhere to a tooth surface cannot be sufficiently removed with conventional whitening agents or abrasives, minute solid matter which adheres to a tooth surface can be removed by using a composition which contains phytic acid and no polyvalent cation and having pH adjusted to a certain range, the tooth can be whitened and gloss can be imparted to the tooth (Patent Document 5).

CITATION LIST

Patent Document

Patent Document 1: JP S56-18913 A
Patent Document 2: JP S56-45407 A
Patent Document 3: JP H11-349460 A
Patent Document 4: JP 2003-335646 A
Patent Document 5: WO 2010/058522 A

SUMMARY OF THE INVENTION

The present invention relates to the following invention.
[1] An oral composition, which comprises the following components (A) and (B):
(A) 0.01 to 3% by mass of phytic acid or a salt thereof, and
(B) 0.01 to 3% by mass of pyrophosphoric acid or a salt thereof, does not comprise a polyvalent cation or comprise a polyvalent cation in an amount of less than 0.1-fold mol relative to phytic acid, has pH 5.5 to 6.5 when diluted with water to 30% by mass, has the mass ratio (B/A) between the component (A) and the component (B) of 0.2 to 3.0, and does not comprise a fluoride or has the fluoride content of less than 500 ppm in terms of fluorine atoms.
[2] A gloss imparting agent for teeth, comprising the oral composition according to [1] above.
[3] A method for imparting gloss to teeth, the method comprising applying the oral composition according to [1] above to teeth.
[4] Use of the oral composition according to [1] above for producing a gloss imparting agent for teeth.
[5] An agent for enhancing a gloss imparting effect on teeth by (A) phytic acid or a salt thereof, the agent comprising (B) pyrophosphoric acid or a salt thereof as an active ingredient, which comprises
(A) 0.01 to 3% by mass of phytic acid or a salt thereof, and
(B) 0.01 to 3% by mass of pyrophosphoric acid or a salt thereof, does not comprise a polyvalent cation or comprises a polyvalent cation in an amount of less than 0.1-fold mol relative to phytic acid, has pH 5.5 to 6.5 when diluted with water to 30% by mass, has the mass ratio (B/A) between the component (A) and the component (B) of 0.2 to 3.0, and does not comprise a fluoride or has the fluoride content of less than 500 ppm in terms of fluorine atoms.
[6] A method for enhancing a gloss imparting effect on teeth by phytic acid, the method comprises applying (B) pyrophosphoric acid or a salt thereof together with (A) phytic acid or a salt thereof to teeth,
wherein a composition for applying (B) pyrophosphoric acid or a salt thereof together with (A) phytic acid or a salt thereof to teeth comprises:
(A) 0.01 to 3% by mass of phytic acid or a salt thereof, and
(B) 0.01 to 3% by mass of pyrophosphoric acid or a salt thereof, does not comprise a polyvalent cation or comprises a polyvalent cation in an amount of less than 0.1-fold mol relative to phytic acid, has pH of 5.5 to 6.5 when diluted with water to 30% by mass, has the mass ratio (B/A) between the component (A) and the component (B) of 0.2 to 3.0, and does not comprise a fluoride or has the fluoride content of less than 500 ppm in terms of fluorine atoms.

DETAILED DESCRIPTION OF THE INVENTION

Figure 1:
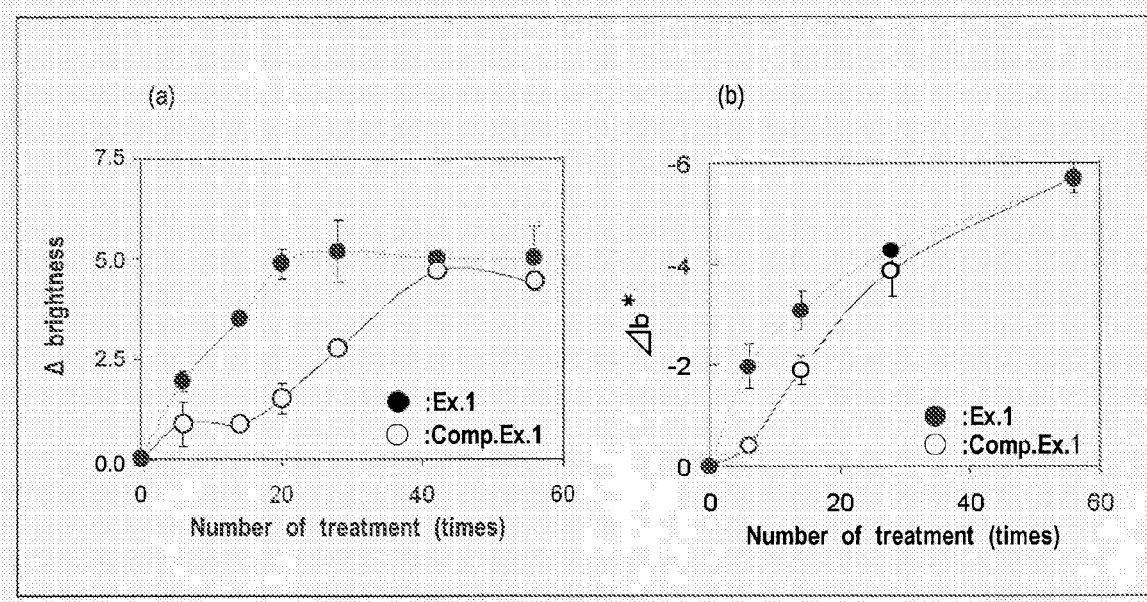
FIG. 1 shows changes in (a) brightness and (b) whiteness (Δb) in Test Example 1.

Although the above conventional composition containing phytic acid has an effect of imparting gloss to teeth, the development of excellent techniques to impart gloss even by short-term use has been demanded.

Therefore, the present invention provides an oral composition having a gloss imparting effect on teeth with excellent fast-acting properties.

Accordingly, the present inventors analyzed components in minute solid matter with a height of less than 1 μm which adheres to a tooth surface in more detail, and found that the components contained not only calcium phosphates but also organic substances. The present inventors further found that a composition, in which phytic acid and pyrophosphoric acid were used in combination, a polyvalent cation was not mixed, pH was in a range of 5.5 to 6.5 and the ratio between phytic acid and pyrophosphoric acid was in a certain range, had an effect of more rapidly removing minute solid matter formed on tooth surfaces and containing the organic substances and calcium phosphates in mix, and a gloss imparting effect was obtained by short term use. The present inventors also found that pyrophosphoric acid or a salt thereof remarkably enhanced a gloss imparting effect on teeth by phytic acid or a salt thereof.

By applying the oral composition of the present invention to teeth, a minute stain removing effect on tooth surfaces and a gloss imparting effect on teeth can be obtained even by short term use.

The present invention will be now described.

(A) Phytic acid or a salt thereof used in the oral composition of the present invention has an excellent tooth whitening action and an excellent gloss imparting action to teeth, the gloss imparting action is remarkably enhanced by concurrently using (B) pyrophosphoric acid or a salt thereof, and an excellent gloss imparting effect can be obtained even by short term use. (B) Pyrophosphoric acid or a salt thereof is effective as an enhancing agent for imparting gloss to teeth by (A) phytic acid or a salt thereof. Phytic acid is also called myo-inositol hexaphosphate, and an inositol phosphate compound. Among various phosphate compounds, phytic acid or a salt thereof is particularly excellent in the gloss imparting effect.

Examples of salts thereof include alkali metal salts such as sodium and potassium, ammonium salts and the like, and alkali metal salts are preferred from the viewpoint of taste and flavor.

The oral composition of the present invention comprises 0.01 to 3% by mass of (A) phytic acid or a salt thereof in the composition. The content of phytic acid or a salt thereof in the composition is 0.01% by mass or more, preferably 0.02% by mass or more, more preferably 0.1% by mass or more from the viewpoint of sufficiently showing an effect of removing minute solid matter and a gloss imparting effect, and preferably 2% by mass or less, more preferably 1.5% by mass or less, even more preferably 1.0% by mass or less from the viewpoint of suppressing decalcification of teeth and from the viewpoint of taste and friction. In addition, the content of phytic acid or a salt thereof is preferably 0.02 to 2% by mass, more preferably 0.02 to 1.5% by mass, even more preferably 0.1 to 1.5% by mass, even more preferably 0.1 to 1.0% by mass in the oral composition. When the oral composition of the present invention is a toothpaste, phytic acid or a salt thereof is preferably comprised in an amount of 0.02 to 1.5% by mass in the toothpaste from the viewpoint of feelings of use such as taste and friction. The content of phytic acid or a salt thereof in the oral composition of the present invention is a value obtained by measuring a total amount by neutralization using potassium hydroxide or sodium hydroxide, and converting it to an acid amount.

A tooth whitening action and a gloss imparting action are enhanced by using (B) pyrophosphoric acid or a salt thereof used in the present invention in combination with (A) phytic acid or a salt thereof. Pyrophosphoric acid is also called diphosphoric acid. Salts of pyrophosphoric acid are preferably alkali metal salts such as a sodium salt and a potassium salt.

The oral composition of the present invention comprises 0.01 to 3% by mass of (B) pyrophosphoric acid or a salt thereof in the composition. The content of pyrophosphoric acid or a salt thereof in the composition is 0.01% by mass or more, preferably 0.02% by mass or more, even more preferably 0.1% by mass or more from the viewpoint of sufficiently showing minute solid matter removing effect, a gloss imparting effect and a whitening effect, and preferably 2% by mass or less, more preferably 1.5% by mass or less, even more preferably 1.0% by mass or less from the viewpoint of taste. In addition, the content of pyrophosphoric acid or a salt thereof is preferably 0.02 to 2% by mass, more preferably 0.02 to 1.5% by mass, even more preferably 0.1 to 1.5% by mass, even more preferably 0.1 to 1.0% by mass in the oral composition. When the oral composition of the present invention is a toothpaste, pyrophosphoric acid or a salt thereof is preferably comprised in an amount of 0.02 to 1.5% by mass in the toothpaste from the viewpoint of feelings of use such as taste. The content of phytic acid or a salt thereof in the oral composition of the present invention is a value obtained by measuring a total amount by neutralization using potassium hydroxide or sodium hydroxide, and converting it to an acid amount.

In the oral composition of the present invention, the contents of the component (A) and the component (B) are each preferably 0.01 to 1.5% by mass and more preferably 0.02 to 1.5% by mass from the viewpoint of obtaining a gloss imparting effect and simultaneously improving taste, and, in addition, more preferably 0.05 to 1.0% by mass, further preferably 0.05 to 0.7% by mass and further preferably 0.1 to 0.7% by mass from the viewpoint of suppressing frictional feel. The total content of the component (A) and the component (B) is preferably 0.02 to 2.5% by mass from the viewpoint of taste, and more preferably 0.1 to 2.0% by mass, even more preferably 0.2 to 1.7% by mass from the viewpoint of suppressing fractional feel.

The mass ratio (B/A) between the component (A) and the component (B) (B/A) in the oral composition of the present invention is important from the viewpoint of the enhancing actions of an effect of removing minute solid matter and a gloss imparting effect and the viewpoint of a tooth whitening action, which is 0.2 to 3.0. The B/A is more preferably 0.2 to 2.0, even more preferably 0.2 to 1.5 from the viewpoint of the fast-acting properties of a gloss imparting effect.

In the oral composition of the present invention, the polyvalent cation content is preferably suppressed to a low level in order to prevent a decrease in solid matter removing effect because polyvalent cations make phytic acid insoluble and reduce solid matter removing effect. The content thereof is measured by ICP emission spectrometry (ICP emission spectrometer: Optima 5300DV manufactured by Perkin Elmer Inc.), and the total content of polyvalent cations is preferably less than 0.1-fold mol relative to phytic acid, more preferably 0.02-fold mol or less. That is, it is desired that agents for mainly supplying polyvalent cations such as aluminum, calcium, magnesium, iron and zinc not be used, and it is preferred that the oral composition substantially contains almost no polyvalent cations.

Since along with cationic antibacterial agents, absorbents such as zeolite and activated carbons reduce solid matter removing effect by phytic acid, the content thereof is preferably less than 0.001% by mass, more preferably 0.0001% by mass or less in the oral composition, and it is preferred that the oral composition not substantially comprise them.

The oral composition of the present invention has pH 5.5 to 6.5 when diluted with water to 30% by mass.

That is, from the viewpoint of removing minute solid matter, suppressing decalcification of tooth surfaces and showing a gloss imparting effect when the composition is applied to the oral cavity, when diluted with water to 30% by mass, the composition has pH 5.5 or more, preferably 5.8 or more, and from the viewpoint of sufficiently showing a gloss imparting effect by solid matter removal, the pH is 6.5 or less, preferably 6.2 or less.

Since the pH of a high viscosity oral composition such as a toothpaste cannot be accurately measured, the pH of a dilution which is obtained by diluting the composition with water to 30% by mass is used as the pH of the composition. The dilution with water to 30% by mass is used to assume the situation of intraoral application of the oral composition. The water is purified water, and distilled water or ion exchanged water is used.

It is preferred to use a pH regulator to adjust the pH of a composition to the above-mentioned range. Examples of pH regulators include organic acids such as acetic acid, fumaric acid, malic acid, lactic acid, gluconic acid and tartaric acid; inorganic acids such as phosphoric acids other than phytic acid and pyrophosphoric acid (e.g. orthophosphoric acid), hydrochloric acid and sulfuric acid; hydroxides such as sodium hydroxide; ammonia or ammonia water, lower alkanolamines, basic amino acids such as arginine and lysine; and the like in a range in which an effect of removing minute solid matter by phytic acid is not inhibited and decalcification of teeth can be suppressed. These may be used individually or two or more may be used in combination. Among these pH regulators, those which are selected from organic acids, inorganic acids other than phytic acid and pyrophosphoric acid and basic amino acids are preferred. Among these pH regulators, the content of organic acids and inorganic acids (excluding phytic acid and pyrophosphoric acid) is preferably 5% or less, more preferably 1% or less relative to phytic acid in the mass ratio from the viewpoint of not inhibiting a gloss imparting effect of phytic acid and pyrophosphoric acid.

It is preferred that the oral composition of the present invention further comprises (C) erythritol. From the viewpoint of imparting gloss and from the viewpoint of suppressing a frictional feel by phosphate compounds, erythritol is preferably comprised in an amount of 1 to 60% by mass. When (C) erythritol is comprised, the content is preferably 1 to 30% by mass, more preferably 3 to 20% by mass in a liquid oral composition. In a dentifrice composition, the (C) erythritol content is preferably 12 to 60% by mass, more preferably 20 to 50% by mass considering a fresh feel and taste obtained by erythritol remaining particles in the composition. In a dentifrice composition, from the viewpoints of feelings of use, a fresh feel and taste, erythritol can be mixed in the form of powder with a particle diameter of less than 35 μm or in the form of particles in the oral composition of the present invention.

As the structures of erythritol, there exist three types of isomer, L-erythritol, D-erythritol and meso-erythritol, and any of the structures can be used in the present invention. Any erythritol which is commonly available can be used, and examples thereof include crystalline erythritol and the like obtained by recrystallization after fermentation of glucose. As crystalline erythritol, commercially available products manufactured by NIKKEN Chemicals Co., Ltd., Mitsubishi-Kagaku Foods Corporation, Cerestar, Inc., Cargill, Incorporated and the like are available. When the particle diameter is large, one with a particle diameter adjusted by pulverization can be used. For the pulverization of erythritol, a roller mill, a hammer mill, a high speed grinder, a pulverizer and the like are commonly used, and erythritol is preferably pulverized by a high speed grinder and a hammer mill because a particle size is easily adjusted and production efficiency is excellent.

When the oral composition of the present invention is a toothpaste, erythritol is desirably dispersed in the toothpaste in the state of powder or particle. Therefore, erythritol is preferably added in the state of powder or particle in the final step of production. From the viewpoint of the long continuation of a cooling feel in the oral cavity, the particle diameter is preferably 45 μm or more and less than 355 μm, more preferably 53 μm or more and less than 300 μm, even more preferably 75 μm or more and less than 250 μm. Erythritol with a particle diameter of 45 μm or more is not instantly dissolved in the mouth and a cooling feel lasts long, which is preferred. Erythritol with a particle diameter of less than 355 μm is easily dissolved in the oral cavity and thus can show a cooling feel.

The particle diameter of erythritol is measured as follows.
Sieve: JIS standard sieve ϕ75 mm
Openings: sieves, each having an opening of 500 μm, 355 μm, 250 μm, 180 μm, 125 μm, 90 μm and 45 μm from top, and a sieve pan under the sieves Shaking machine: electromagnetic micro vibro shifter M-2 (TSUTSU™ SCEINTIFIC INSTRUMENTS CO., LTD.)
Method: on a sieve of 500 μm, 15 g of sample is placed and is classified by the electromagnetic shifter for 5 minutes. The total amount of erythritol on the sieves, each having an opening of 250 μm, 180 μm, 125 μm, 90 μm and 45 μm, is considered as the amount of erythritol with a particle diameter of 45 μm or more and less than 355 μm.

When the oral composition of the present invention comprises (C) erythritol, as the (C) erythritol content, the mass ratio (C/(A+B)) between the component (C) and the sum of the components (A) and (B) is preferably 5 to 1000, more preferably 10 to 800, even more preferably 15 to 500, even more preferably 20 to 500 from the viewpoints of a gloss imparting effect, a fresh feel and feelings of use.

When the oral composition of the present invention is a dentifrice composition and comprises (C) erythritol, the (D) water content is also important, and the (D) water content is preferably 12 to 25% by mass and more preferably 12 to 20% by mass. The mass ratio (C/D) between the component (C) and the component (D) is preferably 1 to 6, more preferably 1 to even more preferably 1.5 to 4 from the viewpoints of a gloss imparting effect, a fresh feel and feelings of use.

In addition, in the oral composition of the present invention, fluorides including sodium monofluorophosphate and fluoride ion supplying compounds such as sodium fluoride, potassium fluoride and ammonium fluoride may be mixed in a range in which a gloss imparting effect by phytic acid or a salt thereof not inhibited (content, dosage form etc.). However, it is preferred that these fluorides not be comprised in the composition, or the fluoride content be preferably less than 500 ppm, more preferably 300 ppm or less in terms of fluorine atoms.

In addition to the above components, for example, a foaming agent, a foaming aid, an abrasive, a humectant, a thickening agent, a gelling agent, a binder, a sweetening agent, a preservative, an antibacterial agent, a medicinally active ingredient, a pigment, a colorant, a flavor and the like are properly contained in the oral composition of the present invention, and the composition can be produced depending on various dosage forms. The combined use with a conventional whitening ingredient such as polyethylene glycol is not also restricted.

The oral composition of the present invention is prepared to a dosage form such as a liquid, a gel or a paste, and used as a dentifrice composition such as a powder dentifrice, a wet dentifrice, a toothpaste or a liquid dentifrice; a liquid oral composition such as a mouthwash; or food such as chewing gum, troche or candy; or a sheet material, cloth, fiber or the like in which the composition is impregnated can be used as a dental hygiene device such as dental floss.

Any dosage form may contain polyethylene glycol, propylene glycol, glycerin, sorbitol, maltitol, xylitol, lactitol or the like for the purpose of a humectant, a thickening agent or the like.

In addition, one or two or more of sodium carboxymethylcellulose, hydroxyethylcellulose, carboxyvinyl polymer, xanthan gum, carrageenan, sodium alginate, hydroxypropyl cellulose, guar gum, sodium chondroitin sulfate and the like can be contained as a thickening agent for liquid compositions or a gelling agent for gel compositions, and further a binder for paste compositions. Among these, binders other than sodium alginate are preferably selected from the viewpoint of sufficiently showing a gloss imparting effect of phytic acid or a salt thereof. Further, a cellulose binder such as sodium carboxymethylcellulose is preferably used in combination with a non-cellulose binder such as xanthan gum from the viewpoint of feelings of use and stability.

In addition, when the salt concentration is high, for example, due to a buffer solution, one or two or more of nonionic polymers, i.e. hydroxyethylcellulose, guar gum, hydroxypropyl cellulose and the like, may be contained.

When the composition of the present invention is a dentifrice composition, the viscosity at 25° C. is preferably 500 to 10000 dPa·s, more preferably 1000 to 7000 dPa·s, even more preferably 1200 to 5000 dPa·s from the viewpoint of a sufficient gloss imparting effect. Here, the viscosity can be measured using a Helipath viscometer at a measuring temperature of 25° C. under measuring conditions of rotor C and the number of revolutions 2.5 r/min for 1 minute.

When the composition of the present invention is a dentifrice composition, granules may be mixed. However, from the viewpoint of suppressing the formation 0 minute roughness on tooth enamel surfaces and not inhibiting gloss formation, it is preferred that granules not be mixed, or granules with the collapse strength of 10 g/granule or less in a dry state and preferably granules with the collapse strength in the coexistence of water of 10 g/granule or less be contained. In addition, an abrasive may be contained in a range in which the gloss imparting effect of the present invention is not inhibited, and for example, silica abrasives such, as hydrous silica, anhydrous silica and silica gel are preferably used.

The application of the oral composition of the present invention to teeth includes both direct application and application in a diluted state to about 30% by mass with e.g. water or saliva. That is, a liquid oral composition like a mouthwash is applied to teeth without dilution. Meanwhile, e.g. a dentifrice composition is applied to teeth in a diluted state to about 30% by mass with saliva.

When such composition is applied to human teeth for 10 seconds to 10 hours (for 10 seconds to 3 minutes for a mouthwash, for 30 seconds to 3 minutes in a case where the composition is dentifrice composition, and for 5 minutes or more for an applicator), for example, once to five times a day, preferably for 1 week to 4 weeks, tooth enamel surfaces are smoothed in a nano-scale without damaging tooth enamel itself by selectively removing nano-scale solid matter (less than 1 μm) on the tooth enamel surfaces, and natural gloss of teeth themselves can be obtained by increasing reflected light from the tooth enamel surfaces. That is, even by long-term use or repeated use, damage on tooth enamel surfaces can be suppressed, and thus teeth with natural luster or gloss can be obtained. In the present invention, can be confirmed that gloss can be obtained by applying the combination of the component (A) and the component (B) e.g. twice a day, 14 to 56 times of application in total (one week to 4 weeks) and it can be further confirmed that gloss can, be obtained by 14 to 28 times of application 1 week to 2 weeks).

Figure 2:
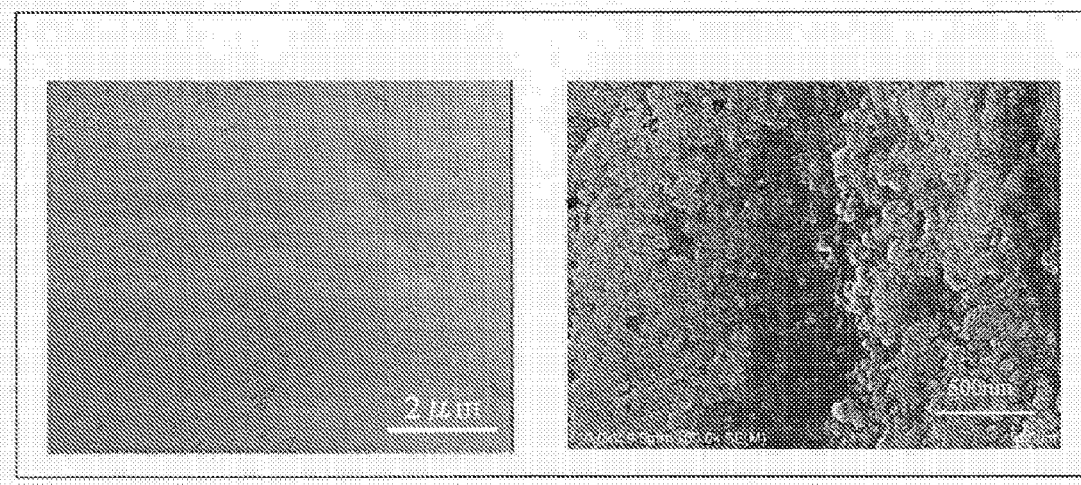
FIG. 2 shows photographs of a tooth surface after treatment in Comparative Example 10, observed with an electron microscope. (a): 50-fold magnification, (b): 50000-fold magnification.

In the present invention, solid matter formed on a tooth surface means a solid with a thickness of less than 1 μm formed on a tooth surface, which can be confirmed by an electron microscope (SEM: HITACHI S-4800). The solid with a thickness of less than 1 μm formed on a tooth surface also includes the aggregate of solids with a thickness of 500 nm or less. As can be seen from a SEM photograph in FIG. 2, this minute solid matter is the sediment of nano-scale solid matter with a thickness of 200 nm or less mostly with a thickness of 100 nm or less wherein the solid matter is thought to be formed by deposition of components such as protein, calcium and phosphorous in saliva and formed by sedimentation of formed deposits. This minute solid matter is deposited and easily formed by the deterioration of an intraoral environment due to aging, a decrease in saliva secretion and the like, and is difficult to remove the solid matter by a common brushing treatment. FIG. 2 is a photograph of a human tooth (extracted tooth) surface, and a SEM photograph obtained after an operation is repeated 28 times, in which brushing is carried out with a toothbrush (Clear Clean multi-care toothbrush, hardness: normal, manufactured by Kao Corporation) while the tooth is immersed in Dentifrice A described in the following Table 1 for 2 minutes, and the tooth is then immersed in artificial saliva at room temperature for 8 hours, FIG. 2 (a) is a SEM photograph of 50-fold magnification and FIG. 2 (b) is a SEM photograph of 50000-fold magnification. As shown in FIG. 2 (a), sediments on the tooth surface are not confirmed on a micro-scale photograph, but sediments on the tooth surface are confirmed on a nano-scale photograph in FIG. 2 (b).

TABLE 1

| Dentifrice A | |
|---|---|
| Sorbitol solution (70%) | 30 |
| Polyethylene glycol (PEG 600) | 5 |
| Sodium saccharin | 0.1 |
| Sodium carboxymethylcellulose | 1.5 |
| Thickening silica | 5 |
| Abrasive silica | 15 |
| Sodium lauryl sulfate | 1.5 |
| Flavor | 1.0 |
| Purified water | balance |
| Total | 100 (mass %) |

As described above, solid matter with a height of less than 1 μm on a tooth surface and further solid matter with a height of 0.5 μm or less can be removed without forming roughness on the tooth surface by using the oral composition of the present invention. Accordingly, excellent gloss is imparted to teeth. Thus, since nano-scale solid matter can be selectively removed without damaging a tooth surface by the composition of the present invention, a remarkable effect that a tooth surface is smoothed and gloss can be imparted is shown.

As described above, the actions to whiten teeth and to impart natural luster and gloss by the composition of the present invention are thought to occur by removing nano-scale solid matter on a tooth enamel surface. It is further thought that the composition of the present invention has an action to reconstruct an interprismatic space by removing products formed in the interprismatic space of the inner part of tooth enamel, and such reconstructive action of the interprismatic space causes a tooth whitening action.

The present invention and preferred embodiments will be now described in detail.

<1> An oral composition, which comprises the following components (A) and (B):
(A) 0.01 to 3% by mass of phytic acid or a salt thereof, and
(B) 0.01 to 3% by mass of pyrophosphoric acid or a salt thereof, does not comprise a polyvalent cation or comprises a polyvalent cation in an amount of less than 0.1-fold mol relative to phytic acid, has pH 5.5 to 6.5 when diluted with water to 30% by mass, has the mass ratio (B/A) between the component (A) and the component (B) of 0.2 to 3.0, and does not comprise a fluoride or has the fluoride content Of less than 500 ppm in terms of fluorine atoms.

<2> An agent for enhancing a gloss imparting effect on teeth by (A) phytic acid or a salt thereof, the agent comprising (B) pyrophosphoric acid or a salt thereof as an active ingredient, which comprises:

(A) 0.01 to 3% by mass of phytic acid or a salt thereof, and (B) 0.01 to 3% by mass of pyrophosphoric acid or a salt thereof, does not comprise a polyvalent cation or comprises a polyvalent cation in an amount of less than 0.1-fold mol relative to phytic acid, has pH 5.5 to 6.5 when diluted with water to 30% by mass, has the mass ratio (B/A) between the component (A) and the component (B) of 0.2 to 3.0, and does not comprise a fluoride or has the fluoride content of less than 500 ppm in terms of fluorine atoms.

<3> A method for enhancing a gloss imparting effect on teeth by phytic acid, the method comprises applying (B) pyrophosphoric acid or a salt thereof together with (A) phytic acid or a salt thereof to teeth, wherein a composition for applying (B) pyrophosphoric acid or a salt thereof together with (A) phytic acid or a salt thereof to teeth comprises:

(A) 0.01 to 3% by mass of phytic acid or a salt thereof, and (B) 0.01 to 3% by mass of pyrophosphoric acid or a salt thereof, does not comprise a polyvalent cation or comprises a polyvalent cation in an amount of less than 0.1-fold mol relative to phytic acid, has pH 5.5 to 6.5 when diluted with water to 30% by mass, has the mass ratio (B/A) between the component (A) and the component (B) of 0.2 to 3.0, and does not comprise a fluoride or has the fluoride content of less than 500 ppm in terms of fluorine atoms.

<4> The oral composition according to <1> above, wherein the component (A) is phytic acid or an alkali metal salt thereof.

<5> The oral composition according to <1> or <4> above, wherein the content of the component (A) is 0.02% by mass or more, preferably 0.1% by mass or more, and 2% by mass or less, preferably 1.5% by mass or less, more preferably 1.0% by mass or less.

<6> The oral composition according to any of <1>, <4> or <5> above, wherein the content of the component (A) is 0.02 to 2% by mass, preferably 0.02 to 1.5% by mass, more preferably 0.1 to 1.5% by mass, even more preferably 0.1 to 1.0% by mass.

<7> The oral composition according to any of <1> and <4> to <6> above, wherein the content of the component (A) is 0.01 to 1.5% by mass, preferably 0.02 to 1.5% by mass, more preferably 0.05 to 1.0% by mass, even more preferably 0.05 to 0.7% by mass, even more preferably 0.1 to 0.7% by mass.

<8> The oral composition according to any of <1> and <4> to <7> above, wherein the content of the component (B) is 0.02% by mass or more, preferably 0.1% by mass or more, and 2% by mass or less, preferably 1.5% by mass or less, more preferably 1.0% by mass or less.

<9> The oral composition according to any of <1> and <4> to <8> above, wherein the content of the component (B) is 0.02 to 2% by mass, preferably 0.02 to 1.5% by mass, more preferably 0.1 to 1.5% by mass, even more preferably 0.1 to 1.0% by mass.

<10> The oral composition according to any of <1> and <4> to <9> above, wherein the content of the component (B) is 0.01 to 1.5% by mass, preferably 0.02 to 1.5% by mass, more preferably 0.05 to 1.0% by mass, even more preferably 0.05 to 0.7% by mass, even more preferably 0.1 to 0.7% by mass.

<11> The oral composition according to any of <1> and <4> to <10> above, wherein the total content of the component (A) and the component (B) is 0.02 to 2.5% by mass, preferably 0.1 to 2.0% by mass, more preferably 0.2 to 1.7% by mass.

<12> The oral composition according to any of <1> and <4> to <11> above, wherein the mass ratio (B/A) between the component (A) and the component (B) is 0.2 to 3.0, preferably 0.2 to 2.0, more preferably 0.2 to 1.5.

<13> The oral composition according to any of <1> and <4> to <12> above, which does not comprise a polyvalent cation or comprises a polyvalent cation in an amount of 0.02-fold mol or less relative to phytic acid.

<14> The oral composition according to any of <1> and <4> to <13> above, wherein the oral composition does not comprise a cationic antibacterial agent or has the content of the cationic antibacterial agent of less than 0.001% by mass, preferably less than 0.0001% by mass.

<15> The oral composition according to any of <1> and <4> to <14> above, wherein the oral composition has pH 5.8 or more or 6.2 or less when diluted with water to 30% by mass.

<16> The oral composition according to any of <1> and <4> to <15> above, which comprises a pH regulator, wherein the pH regulator is selected from the group consisting of an organic acid and inorganic acid excluding phytic acid and pyrophosphoric acid, and the content thereof is preferably 5% or less relative to phytic acid in the mass ratio, more preferably 1% or less.

<17> The oral composition according to any of <1> and <4> to <16> above, which further comprises the component (C), erythritol, wherein the mass ratio (C/(A+B)) between the component (C) and the sum of the components (A) and (B) is 5 to 1000, preferably 10 to 800, more preferably 15 to 500, even more preferably 20 to 500.

<18> The oral composition according to any of <1> and <4> to <17> above, which further comprises the component (D), water, in an amount of 12 to 25% by mass and preferably 12 to 20% by mass, wherein the mass ratio (C/D) between the components (C) and (D) is 1 to 6, preferably 1 to 5, more preferably 1.5 to 4.

<19> The oral composition according to any of <1> and <4> to <18> above, wherein the oral composition does not comprise a fluoride or has the fluoride content of 300 ppm or less in terms of fluorine atoms.

<20> The oral composition according to any of <1> and <4> to <19> above, wherein the oral composition is a dentifrice composition, and the viscosity at 25° C. is preferably 500 to 10000 dpa·s, more preferably 1000 to 7000 dpa·s, even more preferably 1200 to 5000 dpa·s.

<21> A gloss imparting agent for teeth, comprising the oral composition according to any of <1> and <4> to <20> above.

<22> A method for imparting gloss to teeth, the method comprising applying the oral composition according to any of <1> and <4> to <20> above to teeth.

<23> Use of the oral composition according to any of <1> and <4> to <20> above for producing a gloss imparting agent for teeth.

<24> The agent for enhancing a gloss imparting effect on teeth by (A) phytic acid or a salt thereof, the agent comprising (B) pyrophosphoric acid or a salt thereof as an active ingredient according to <2> above, wherein the agent is the oral composition according to any of <4> to <20> above.

<25> The method for enhancing a gloss imparting effect on teeth by phytic acid, the method comprising applying (B) pyrophosphoric acid or a salt thereof together with (A) phytic acid or a salt thereof to teeth according to <3>, wherein the composition for applying (B) pyrophosphoric acid or a salt thereof together with (A) phytic acid or a salt thereof to teeth is the oral composition according to any of <4> to <20> above.

EXAMPLES

In the following Examples, % means % by mass.

Test Example 1

A toothpaste (Example 1) comprising phytic acid and pyrophosphoric acid shown in Table 2 and a toothpaste (Comparative Example 1) not comprising pyrophosphoric acid were produced. In toothpastes in Example 1 and Comparative Example 1, polyvalent cations were not substantially mixed, and polyvalent cations such as magnesium, aluminum and calcium in test solutions were measured by IPC emission spectrometry and were less than 0.02-fold mol relative to phytic acid. The pHs of Example 1 and Comparative Example 1 are measured values when diluted with ion exchanged water to 30% by mass.

TABLE 2

|  | Example 1 | Comparative Example 1 |
| --- | --- | --- |
| Phytic acid | 0.3 | 0.3 |
| Pyrophosphoric acid | 0.4 | — |
| Erythritol | 40.0 | 40.0 |
| Glycerin | 8.0 | 8.0 |
| Sorbitol solution (70%) | 25.0 | 25.0 |
| Polyethylene glycol 600 | 3.0 | 3.0 |
| Silicic anhydride | 10.0 | 10.0 |
| Sodium carboxymethylcellulose | 0.6 | 0.6 |
| Xanthan gum | 0.1 | 0.1 |
| Sodium saccharin | 0.05 | 0.05 |
| Sodium lauryl sulfate | 1.5 | 1.5 |
| Flavor | 1.0 | 1.0 |
| pH regulator (sodium hydroxide) | q.s. | q.s. |
| Purified water | balance | balance |
| Total | 100.0 | 100.0 |
| pH (*1) | 6 | 6 |

(*1) pH when diluted to 30% by mass (Treatment Method)

Extracted toothpastes in Example 1 and Comparative Example 1, and brightness and whiteness before treatment and after several times of treatments were measured by methods described below.

Treatment with toothpastes was carried out using treatment liquids which were prepared by diluting toothpastes in Example 1 and Comparative Example 1 to 30% by mass at room temperature (25° C.) by the following procedure. Extracted teeth were soaked in ion exchanged water for washing, and immersed in a treatment liquid which is prepared by diluting the toothpaste to 30% by mass for 5 minutes. Next, extracted teeth removed from the treatment liquid were washed with ion exchanged water, and immersed in artificial saliva for approximately 3 hours. This operation was considered as a single treatment, and the treatment was carried out up to 56 times. The brightness and b* after 7 times, 14 times, 21 times, 28 times, 42 times and 56 times of treatments were measured by the following methods. Extracted teeth were human teeth, and three teeth which were not treated to remove stains by e.g. abrasion were used for each treatment liquid. As the artificial saliva, an aqueous solution of calcium chloride (1.0 mM), potassium hydrogen phosphate (0.9 mM) and HEPES (4-(2-hydroxyethyl)-1-piperazineethanesulfonic acid) (2.0 mM) was adjusted to pH of 7 by potassium hydroxide and used. Three extracted teeth were used, and Δbrightness and Δb* were evaluated by the average measured value of three extracted teeth.

(Method for Measuring Brightness)

As a method for measuring brightness, a method, in which surface reflected light intensity is measured by image analysis using polarized light, was used. As a device for taking an evaluation image, a digital single-lens reflex camera Nikon D70 as a camera, Ai AF Micro-Nikkor 105 mm F2.8D as a lens and Wireless Remote Speedlight SB-R200 as a stroboscopic light source (both manufactured by Nikon Corporation) were combined and used. Plastic polarizing film (manufactured by Edmund Optics Inc.) were arranged in front of the light-emitting part of Speedlight and the lens so that the transmission axes would be crossed at a 30-degree angle, and photographs were taken. The average brightness of a highlight part was calculated from the photo image using Adobe Photoshop CS3 (manufactured by Adobe Systems Incorporated). A higher value of brightness means higher gloss. The difference in brightness before treatment and after treatment by an oral composition (brightness after treatment−brightness before treatment) was used as Δbrightness, and a higher value of Δbrightness means an increase in gloss.

(Evaluation of Whiteness)

The image taken using a digital camera D1x (manufactured by Nikon Corporation) and a white flash light source (manufactured by Konica Minolta, Inc.) was expressed by the L*a*b* color system using Adobe Photoshop (manufactured by Adobe Systems Incorporated), and the whiteness of teeth (extracted teeth) was evaluated by the value of b*. The Δb* means a difference in b* before treatment and after treatment by an oral composition {(b* after treatment)−(b* before treatment)}. A value of b* closer to 0 means less yellowish, and whiter color, and a lower value of Δb*, i.e. a higher absolute value of Δb*, means whiter color.

FIG. 1 shows changes of differences in brightness (Δbrightness) (a) and differences in whiteness (Δb*) (b) before treatment and after several times of treatment with toothpastes in Example 1 and Comparative Example 1 for each time of the treatment. As shown in FIG. 1, the toothpaste in Example 1 has Lowe Δbrightness than that of the toothpaste in Comparative Example 1 at fewer times of treatment, that is, −Δb* (the absolute value of Δb*) is high. It is confirmed that by using the component (A) and the component (B) in combination, a gloss imparting effect on teeth and a whitening effect can be obtained by fewer times of treatment.

Test Example 2

Effect by Using Phytic Acid and Other Phosphate Compounds in Combination

Table 3 shows components of liquid oral compositions comprising phytic acid and pyrophosphoric acid, tripolyphosphoric acid or orthophosphoric acid and their contents. A liquid oral composition in which these components were blended (Example 2) was prepared as a test solution. In the liquid oral composition in Example 2, polyvalent cations were not substantially mixed, and polyvalent cations such as magnesium, aluminum and calcium in the test solution were measured by IPC emission spectrometry and were less than 0.02-fold mol relative to phytic acid. Comparative Example 5 is a mouthwash with pH 7.0, and in Comparative Examples 6 and 7, magnesium chloride is mixed as a polyvalent cation, and the polyvalent cation is comprised in an amount of approximately 13-fold mol relative to phytic acid.

The pH of the test solution is pH when diluted with ion exchanged water to 30% by mass. Teeth used for the test were extracted teeth (human teeth), and those which were not treated to remove stains by e.g. abrasion were used.

A brushing treatment with test solutions of liquid oral compositions shown in Table 3 was carried out by the following procedure.

Extracted teeth were immersed in ion exchanged water for washing, and brushing was carried out with a toothbrush (Clear Clean multi-care toothbrush, hardness: normal, manufactured by Kao Corporation) while the extracted teeth were immersed in each test solution at room temperature (25° C.) for 2 minutes. After that, the extracted teeth were immersed in ion exchanged water for washing, and immersed in artificial saliva at room temperature (25° C.) for 3 hours. After this cycle was carried out 24 times and 48 times, brightness and b* were measured by the same method as in Test Example 1, and differences in brightness and b* between before and after treatment (Δbrightness, Δb*) were calculated. The results are shown in Table 3. The same artificial saliva as in Test Example 1 was used. Three extracted teeth were used, and Δbrightness and Δb* were evaluated by the average measured value of three extracted teeth.

The surface conditions of extracted teeth were evaluated by observing the teeth after the above-mentioned 24 times and 48 times of treatment using a loupe (10-fold magnification) with the naked eye.

Figure 3:
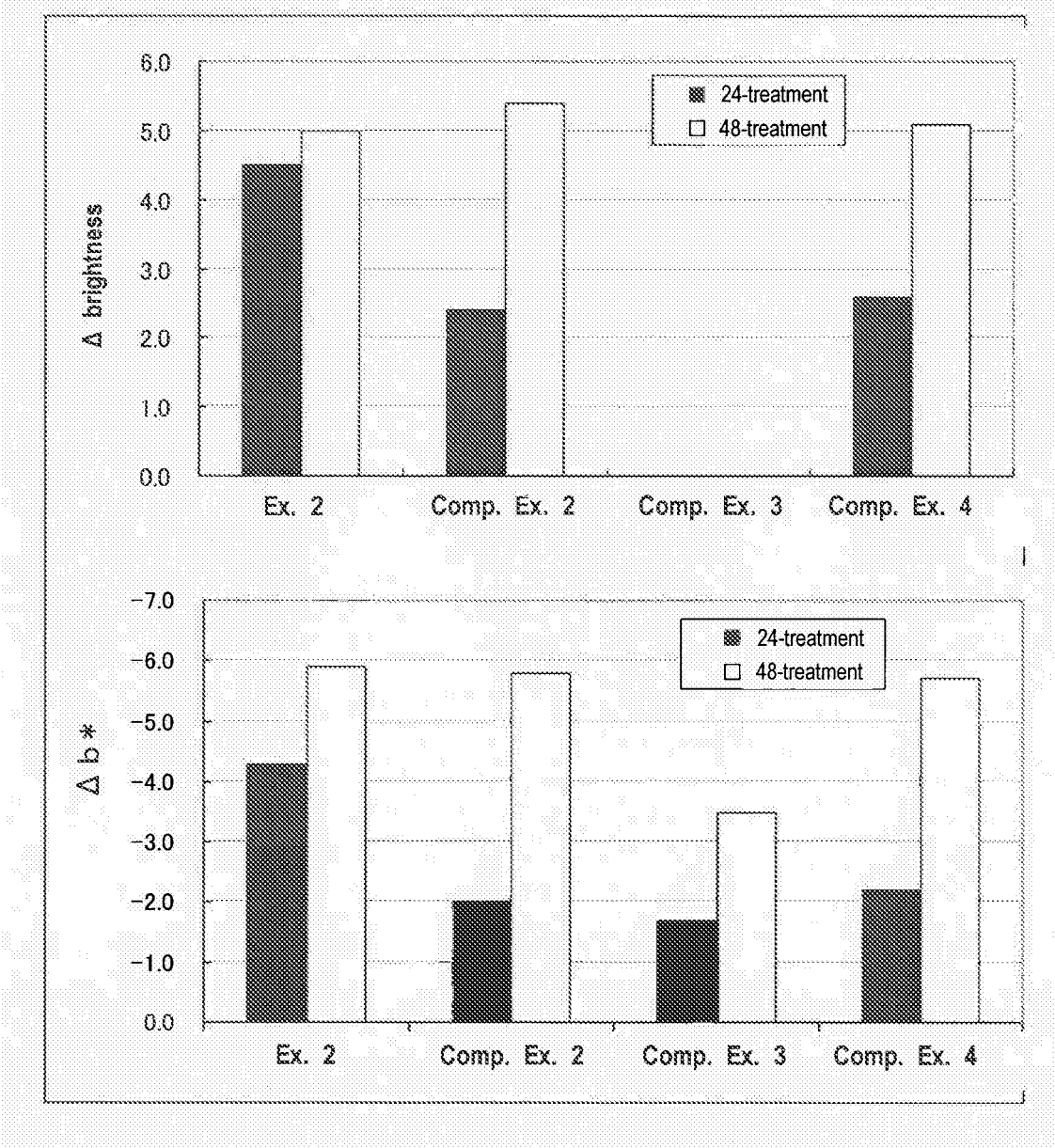
FIG. 3 shows changes in brightness and whiteness (Δb) in Test Example 2.

Table 3 shows Δbrightness, Δb* and the surface conditions of teeth after 24 times and 48 times of treatment, and FIG. 3 shows Δbrightness after 24 times of treatment in Example 2 and Comparative Examples 2 to 4.

TABLE 3

|  |  | Example 2 | Comparative Example 2 | Comparative Example 3 | Comparative Example 4 | Comparative Example 5 | Comparative Example 6 | Example 3 | Comparative Example 7 |
|---|---|---|---|---|---|---|---|---|---|
|  | Phytic acid | 1.0 | 1.0 | 1.0 | 1.0 | 1.0 | 1.0 | 0.5 | 0.5 |
|  | Pyrophosphoric acid | 1.0 | — | — | — | 1.0 | — | 0.5 | 0.5 |
|  | Tripolyphosphoric acid | — | — | 1.0 | — | — | — | — | — |
|  | Orthophosphoric acid | — | — | — | 1.0 | — | — | — | — |
|  | Magnesium chloride | — | — | — | — | — | 4.0 | — | 4.0 |
|  | Purified water | balance | balance | balance | balance | balance | balance | balance | balance |
|  | Total | 100 | 100 | 100 | 100 | 100 | 100 | 100 | 100 |
|  | pH (*1) | 6.0 | 6.0 | 6.0 | 6.0 | 7.0 | 6.0 | 6.0 | 6.0 |
| 24 Times of treatment | Δbrightness | 4.5 | 2.4 | <0 | 2.6 | 2.1 | 1.4 | 4.7 | 2.2 |
| | Δb* | −4.3 | −2.0 | −1.7 | −2.2 | −1.7 | −1.3 | −4.5 | −1.6 |
| | Surface conditions observed by loupe | Smooth | Smooth | Slightly rough surface | Smooth | Solid matter before the test remains | Solid matter before the test remains | Smooth | Solid matter before the test remains |
| 48 Times of treatment | Δbrightness | 5.0 | 5.4 | <0 | 5.1 | 2.3 | 2.1 | 5.1 | 2.3 |
| | Δb* | −5.9 | −5.8 | −3.5 | −5.7 | −2.1 | −1.8 | −6.1 | −1.9 |
| | Surface conditions observed by loupe | Smooth | Smooth | Rough surface | Smooth | Solid matter before the test remains | Solid matter before the test remains | Smooth | Solid matter before the test remains |

(*1): pH when diluted to 30% by mass

As can be seen from Table 3 and FIG. 3, when phytic acid and pyrophosphoric acid were combined, the gloss imparting effect and the whitening effect were improved, but when phytic acid and tripolyphosphoric acid or orthophosphoric acid were combined, the gloss imparting effect and the whitening effect were not sufficiently obtained by 24 times of treatment. In Comparative Example 5 with pH 7.0 and Comparative Examples 6 and 7 comprising a polyvalent cation, the gloss imparting effect and the whitening effect were not obtained.

In Example 2 in which phytic acid and pyrophosphoric acid were combined, a high gloss imparting effect and a high whitening effect were confirmed by fewer times of treatment, i.e. 24 times of treatment, as compared to Comparative Example 2 which did not have the combination and used only phytic acid.

Test Example 3

Content Ratio Between Phytic Acid and Pyrophosphoric Acid

As shown in Table 4, liquid oral compositions in which the concentrations of phytic acid and pyrophosphoric acid were changed were produced, and tested in the same manner as in Test Example 2. The results are shown in Table 4 and FIG. 4.

TABLE 4

|  | | Example 2 | Example 4 | Example 5 | Example 6 | Example 7 | Example 8 | Example 9 | Example 10 | Comparative Example 8 | Comparative Example 10 |
|---|---|---|---|---|---|---|---|---|---|---|---|
| | Phytic acid (A) | 1.0 | 0.3 | 0.3 | 0.3 | 0.3 | 1.0 | 0.05 | 0.1 | 0.3 | 0.3 |
| | Pyrophosphoric acid (B) | 1.0 | 0.1 | 0.3 | 0.4 | 0.6 | 3.0 | 0.05 | 0.1 | 1.0 | 3.0 |
| | Purified water | balance | balance | balance | balance | balance | balance | balance | balance | balance | balance |
| | Total | 100 | 100 | 100 | 100 | 100 | 100 | 100 | 100 | 100 | 100 |
| | (B)/(A) | 1.0 | 0.3 | 1.0 | 1.3 | 2.0 | 3.0 | 1.0 | 1.0 | 3.3 | 10.0 |
| | pH (*1) | 6.0 | 6.0 | 6.0 | 6.0 | 6.0 | 6.0 | 6.0 | 6.0 | 6.0 | 6.0 |
| 24 Times of treatment | Δbrightness | 4.5 | 4.5 | 4.6 | 4.8 | 4.2 | 3.7 | 4.1 | 4.2 | 2.1 | 1.3 |
| | Δb* | −4.3 | −4.3 | −4.6 | −4.8 | −4.0 | −3.9 | −4.0 | −4.2 | −2.7 | −0.6 |
| | Surface conditions observed by loupe | Smooth | Smooth | Smooth | Smooth | Smooth | Smooth | Smooth | Smooth | Smooth | Slightly rough surface |
| 48 Times of treatment | Δbrightness | 5.0 | 5.1 | 5.2 | 5.3 | 4.8 | 4.4 | 4.5 | 4.8 | 3.0 | 1.9 |
| | Δb* | −5.9 | −5.9 | −6.0 | −6.0 | −5.2 | −4.5 | −4.5 | −4.8 | −3.5 | −1.0 |
| | Surface conditions observed by loupe | Smooth | Smooth | Smooth | Smooth | Smooth | Smooth | Smooth | Smooth | Smooth | Slightly rough surface |

(*1): pH when diluted to 30% by mass

Figure 4:
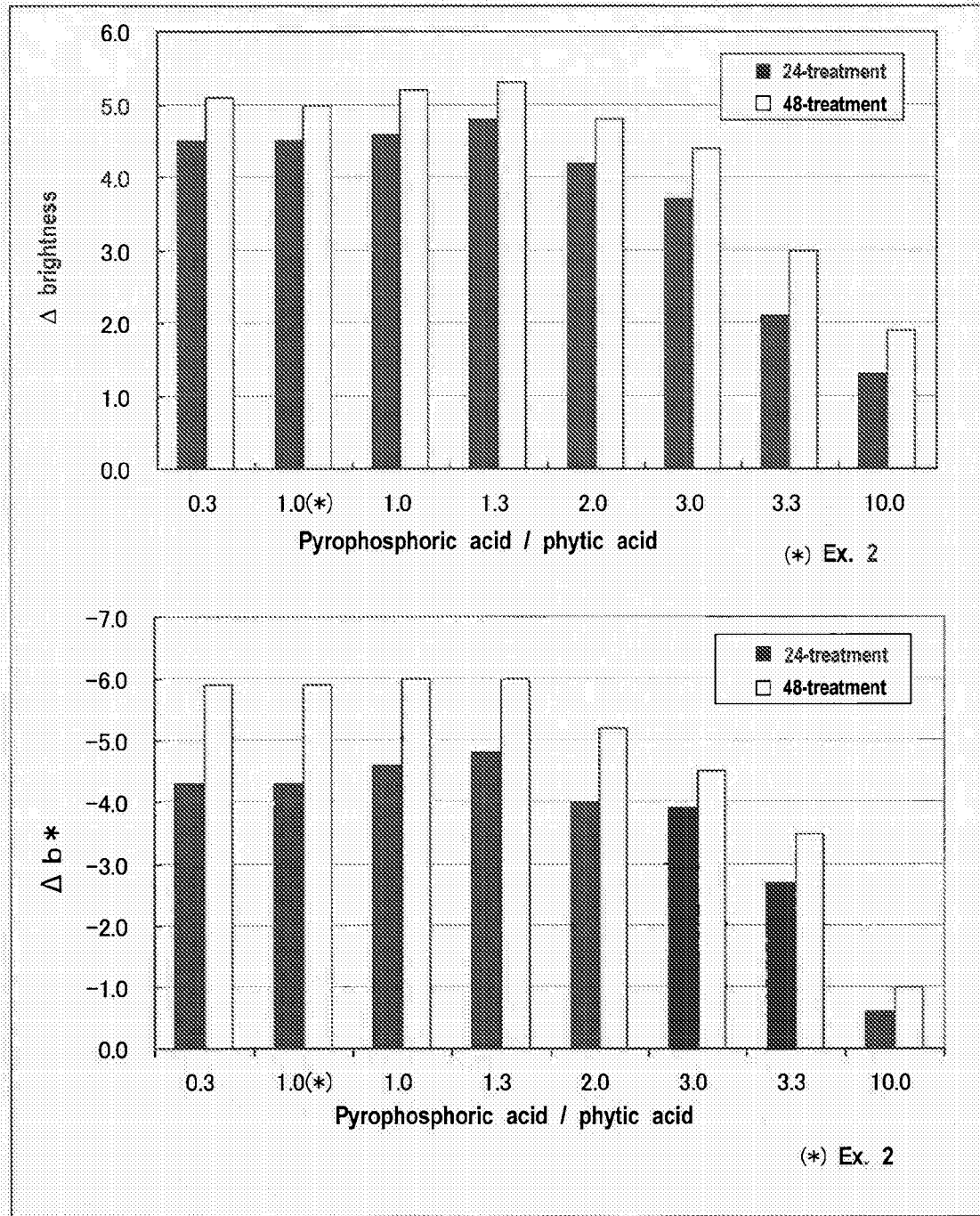
FIG. 4 shows changes in brightness and whiteness (Δb) in Test Example 3.

As can be seen from Table 4 and FIG. 4, it was confirmed that when the ratio of (B) pyrophosphoric acid/(A) phytic acid was 0.2 to 3.0, an excellent gloss imparting effect and an excellent whitening effect were obtained.

Test Example 4

Liquid oral compositions shown in Table 5 were produced, and tested in the same manner as in Test Example 2 Taste as also evaluated. Three panels evaluated taste by gargling with liquid oral compositions. The results obtained by discussion of the three panels are shown in Table 5.

TABLE 5

|  | | Example 2 | Example 8 | Example 11 |
|---|---|---|---|---|
| | Phytic acid (A) | 1.0 | 1.0 | 1.0 |
| | Pyrophosphoric acid (B) | 1.0 | 3.0 | 0.5 |

TABLE 5-continued

|  | | Example 2 | Example 8 | Example 11 |
|---|---|---|---|---|
| | Purified water | balance | balance | balance |
| | Total | 100 | 100 | 100 |
| | pH (*1) | 6.0 | 6.0 | 6.0 |
| | (A) + (B) | 2.0 | 4.0 | 1.5 |
| 24 Times of treatment | Δbrightness | 4.5 | 3.7 | 4.6 |
| | Δb* | −4.3 | −3.9 | −4.4 |
| | Surface conditions observed by loupe | Smooth | Smooth | Smooth |
| 48 Times of treatment | Δbrightness | 5.0 | 4.4 | 5.0 |
| | Δb* | −5.9 | −4.5 | −5.8 |
| | Surface conditions observed by loupe | Smooth | Smooth | Smooth |
| | Taste (salty taste) | Slightly salty taste | Strongly salty taste | No salty taste |

*pH when diluted to 30% by mass

As shown in Table 5, it is confirmed that when the total content of (A phytic acid and (B) pyrophosphoric acid was above 3.0, a salty taste was strong.

Test Example 5

Liquid oral compositions shown in Table 6 were produced, and tested in the same manner as in Test Example 2. A frictional feel was also evaluated. Three panels evaluated the frictional feel by gargling with liquid oral compositions. The results obtained by discussion of the three panels are shown in Table 6.

TABLE 6

|  | Example 3 | Example 12 | Example 13 |
|---|---|---|---|
| Phytic acid (A) | 0.5 | 0.5 | 1.5 |
| Pyrophosphoric acid (B) | 0.5 | 0.5 | 1.5 |

TABLE 6-continued

|  |  | Example 3 | Example 12 | Example 13 |
|---|---|---|---|---|
|  | Erythritol | — | 20.0 | — |
|  | Purified water | balance | balance | balance |
|  | Total | 100 | 100 | 100 |
|  | (A) + (B) | 1.0 | 1.0 | 3.0 |
|  | pH (*1) | 6.0 | 6.0 | 6.0 |
| 24 Times of treatment | Δbrightness | 4.7 | 4.9 | 4.3 |
|  | Δb* | −4.5 | −4.4 | −4.3 |
|  | Surface conditions observed by loupe | Smooth | Smooth | Smooth |
| 48 Times of treatment | Δbrightness | 5.1 | 5.4 | 4.9 |
|  | Δb* | −6.1 | −6.2 | −5.6 |
|  | Surface conditions observed by loupe | Smooth | Smooth | Smooth |
|  | Frictional feel | Slight frictional feel of teeth, but negligible | No frictional feel of teeth | Strong frictional feel of teeth |

*pH when diluted to 30% by mass

As can be seen from Table 6, it is found that when erythritol is mixed along with phytic acid and pyrophosphoric acid, a gloss imparting effect is excellent and frictional feel of teeth is inhibited.

The invention claimed is:

1. An oral composition, which comprises the following components (A) and (B):
   (A) 0.01 to 3% by mass of phytic acid or a salt thereof, and
   (B) 0.01 to 3% by mass of pyrophosphoric acid or a salt thereof, does not comprise a polyvalent cation or comprises a polyvalent cation selected from the group consisting of aluminum, calcium, magnesium, iron and zinc in an amount of less than 0.1-fold mol relative to phytic acid, has a pH of 5.5 to 6.5 when diluted with water to 30% by mass, has a mass ratio (B/A) between the component (A) and the component (B) of 0.2 to 3.0, and does not comprise a fluoride or has a fluoride content of less than 500 ppm in terms of fluorine atoms.

2. The oral composition according to claim 1, wherein the content of the component (A) is 0.02 to 2% by mass, and the content of the component (B) is 0.02 to 2% by mass.

3. The oral composition according to claim 1, wherein the content of the component (A) is 0.01 to 1.5% by mass, the content of the component (B) is 0.01 to 1.5% by mass and the total content of the component (A) and the component (B) is 0.02 to 2.5% by mass.

4. The oral composition according to claim 1, which further comprises a pH regulator selected from the group consisting of organic acids and inorganic acids but excluding phytic and pyrophosphoric acid, wherein the pH regulator is 5% or less relative to phytic acid in the mass ratio.

5. The oral composition according to claim 1, which further comprises component (C), erythritol, wherein the mass ratio (C/(A+B)) between the component (C) and the sum of the components (A) and (B) is 5 to 1000.

6. The oral composition according to claim 5, which further contains component (D), water, in an amount of 12 to 25% by mass, wherein the mass ratio (C/D) between the components (C) and (D) is 1 to 6 and the oral composition is a dentifrice.

7. The oral composition according to claim 5, wherein the component (C), erythritol, content is 12 to 60% by mass and the oral composition is a dentifrice.

8. The oral composition according to claim 1, wherein the oral composition does not comprise a fluoride or has a fluoride content of 300 ppm or less in terms of fluorine atoms.

9. The oral composition according to claim 1, wherein the oral composition does not comprise a cationic antibacterial agent or has a cationic antibacterial agent content of less than 0.001% by mass.

10. The oral composition according to claim 1, wherein the component (A) is phytic acid or an alkali metal salt thereof.

11. A method for imparting gloss to teeth, comprising applying an oral composition to teeth, wherein the composition comprises the following components (A) and (B):
    (A) 0.01 to 3% by mass of phytic acid or a salt thereof, and
    (B) 0.01 to 3% by mass of pyrophosphoric acid or a salt thereof, does not comprise a polyvalent cation or comprises a polyvalent cation selected from the group consisting of aluminum, calcium, magnesium, iron and zinc in an amount of less than 0.1-fold mol relative to phytic acid, has a pH of 5.5 to 6.5 when diluted with water to 30% by mass, has a mass ratio (B/A) between the component (A) and the component (B) of 0.2 to 3.0, and does not comprise a fluoride or has a fluoride content of less than 500 ppm in terms of fluorine atoms.

12. The method for imparting gloss to teeth according to claim 11, wherein the content of the component (A) is 0.02 to 2% by mass, and the content of the component (B) is 0.02 to 2% by mass in the composition.

13. The method for imparting gloss to teeth according to claim 11, wherein the content of the component (A) is 0.01 to 1.5% by mass, the content of the component (B) is 0.01 to 1.5% by mass and the total content of the component (A) and the component (B) is 0.02 to 2.5% by mass in the composition.

14. The method for imparting gloss to teeth according to claim 11, which further comprises a pH regulator selected from the group consisting of organic acids and inorganic acids but excluding phytic acid and pyrophosphoric acid, wherein the pH regulator is 5% or less relative to phytic acid in the mass ratio.

15. The method for imparting gloss to teeth according to claim 11, wherein the composition further comprises component (C), erythritol and the mass ratio (C/(A+B)) between the component (C) and the sum of the components (A) and (B) is 5 to 1000.

16. The method for imparting gloss to teeth according to claim 15, wherein the composition further comprises component (D), water, in an amount of 12 to 25% by mass, wherein the mass ratio (C/D) between the components (C) and (D) is 1 to 6 and the oral composition is a dentifrice.

17. The method for imparting gloss to teeth according to claim 15, wherein the composition is a dentifrice and the content of the component erythritol is 12 to 60% by mass.

18. The method for imparting gloss to teeth according to claim 11, wherein the oral composition does not comprise a fluoride or has the fluoride content of 300 ppm or less in terms of fluoride atoms.

19. The method for imparting gloss to teeth according to claim 11, wherein the oral composition does not comprise a cationic antibacterial agent or has a cationic antibacterial agent content of less than 0.001% by mass.

20. The method for imparting gloss to teeth according to claim 11, wherein the component (A) is phytic acid or an alkali metal salt thereof.

* * * * *